US00PP36345P2

(12) United States Plant Patent
Saito et al.

(10) Patent No.: US PP36,345 P2
(45) Date of Patent: Dec. 31, 2024

(54) GRAPEVINE PLANT NAMED 'SUNNY HEART'

(50) Latin Name: ***Vitis labrusca* L. x *Vitis vinifera* L.**
Varietal Denomination: SUNNY HEART

(71) Applicant: NATIONAL AGRICULTURE AND FOOD RESEARCH ORGANIZATION, Ibaraki (JP)

(72) Inventors: Toshihiro Saito, Higashihiroshima (JP); Akihiko Sato, Aridagawa-cho (JP); Atsushi Kono, Tsukuba (JP); Noriyuki Onoue, Higashihiroshima (JP); Nobuhito Mitani, Tsukuba (JP); Akifumi Azuma, Tsukuba (JP); Yusuke Ban, Higashihiroshima (JP); Masahiko Yamada, Ishioka (JP); Toshihito Ueno, Katsunuma-cho (JP); Mikio Shiraishi, Chikushino (JP); Takeo Shimizu, Tsukubamirai (JP); Ryusuke Matsuzaki, Takehara (JP); Ikuko Nakajima, Tsukuba (JP); Taketoshi Ueno, Takehara (JP); Takao Ito, Higashihiroshima (JP); Takashi Haji, Tsukuba (JP); Yuya Chiaki, Tsukuba (JP)

(73) Assignee: NATIONAL AGRICULTURE AND FOOD RESEARCH ORGANIZATION, Tsukuba (JP)

( * ) Notice: Subject to any disclaimer, the term of this patent is extended or adjusted under 35 U.S.C. 154(b) by 0 days.

(21) Appl. No.: 18/584,909

(22) Filed: Feb. 22, 2024

(30) Foreign Application Priority Data

Nov. 13, 2023 (JP) ..... PVP37121

(51) Int. Cl.
*A01H 5/08* (2018.01)
*A01H 6/88* (2018.01)

(52) U.S. Cl.
USPC ..... Plt./206

(58) Field of Classification Search
USPC ..... Plt./205, 206
See application file for complete search history.

*Primary Examiner* — Susan McCormick Ewoldt
(74) *Attorney, Agent, or Firm* — Seckel IP, PLLC

(57) ABSTRACT

A new variety of grapevine 'SUNNY HEART' that has green leaves and berries having a broad ellipsoid shape, red skin, and muscat flavor.

6 Drawing Sheets

Common name: Grapevine.

Botanical classification: *Vitis labrusca* L. x *Vitis vinifera* L.

Variety denomination: 'SUNNY HEART'.

CROSS-REFERENCE TO RELATED APPLICATION

This application claims priority of Japanese plant variety rights application No. 37121 filed Nov. 13, 2023, the entire content of which is incorporated by reference herein.

BACKGROUND OF THE NEW VARIETY

The present invention relates to a new and distinct variety of grapevine, *Vitis labrusca* L. x *Vitis vinifera* L., which has been given the variety denomination 'SUNNY HEART'.

This new grapevine has green young leaves, R.H.S. Colour Chart: 148C, and berries having a broad ellipsoid shape, red skin, and muscat flavor, that distinguish it, notably from its male parent 'SHINE MUSCAT' (berries having yellow green skin) and female parent '626-84' (berries having dark red violet skin and sharp brisk flavor), as well as from reference varieties 'SEKIREI' (reddish young leaves, R.H.S. Colour Chart: 183B, 144A, berries having narrow ellipsoid shape and pale red skin) and 'KOTOPY' (greenish-red young leaves, R.H.S. Colour Chart: 148C, 178B, berries having narrow ellipsoid shape and pale red skin).

ORIGIN OF THE VARIETY

The parent varieties are 'SHINE MUSCAT' (male parent) (not patented in the U.S.) and '626-84' (female parent) (not patented in the U.S.), respectively.

The variety was developed and propagated in Akitsu, Hiroshima, Japan.

The variety was reproduced asexually in Akitsu, Hiroshima, Japan by vegetative reproduction by grafting one-year-old cuttings on rootstocks.

In 2004, seedlings from crossing the parent varieties and collecting seeds were grown.

In 2007, they were grafted on root stock.

In 2009, the first fruit was harvested and lines were selected having fruit with good taste.

In 2016, plants were selected and named 'Akitsu 32' as temporary name for purposes of confidential testing for local adaptability.

In 2018-2022, growing tests were performed under confidentiality conditions at thirty-seven testing stations in Japan.

In 2022, budding and berry ripening times were measured.

On Nov. 13, 2023, an application for plant variety rights No. 37121 was filed for the present variety in the Japanese Plant Variety Protection Office of the Ministry of Agriculture, Forestry and Fisheries (MAFF), Japan.

Cultivation of the variety does not require special conditions or treatments.

The variety is currently mainly intended for fruit production (table grape).

SUMMARY OF THE VARIETY

The variety is distinguished by green young leaves, R.H.S. Colour Chart: 148C, and berries having a broad ellipsoid shape, red skin, and muscat flavor, that distinguish it, notably from its male parent 'SHINE MUSCAT' (berries having yellow green skin) and female parent '626-84' (berries having dark red violet skin and sharp brisk flavor), as well as from reference varieties 'SEKIREI' (reddish young leaves, R.H.S. Colour Chart: 183B, 144A, berries having narrow ellipsoid shape and pale red skin) and 'KOTOPY' (greenish-red young leaves, R.H.S. Colour Chart: 148C, 178B, berries having narrow ellipsoid shape and pale red skin).

A comparison with the male parent 'SHINE MUSCAT' is as follows (evaluation based on averages):

TABLE 1

| No. | Characteristics | Male parent 'SHINE MUSCAT' States | Present variety 'SUNNY HEART' States |
|---|---|---|---|
| 59 | Mature leaf: depth of upper lateral sinuses | medium | shallow |
| 63 | Mature leaf: ratio length/width of teeth | medium | small |
| 91 | Berry: color of skin (without bloom) | yellow green (RHS 146C) | Red (RHS 187B) |

A comparison with the female parent '626-84' is as follows (evaluation based on averages):

TABLE 2

| No. | Characteristics | Female parent '626-84' States | Present variety 'SUNNY HEART' States |
|---|---|---|---|
| 91 | Berry: color of skin (without bloom) | dark red violet (RHS 184B) | Red (RHS 187B) |
| 101 | Berry: particular flavor | sharp brisk | Muscat |

A comparison with the reference varieties 'SEKIREI' is as follows (evaluation based on averages):

TABLE 3

| No. | Characteristics | Reference variety 'SEKIREI' States | Present variety 'SUNNY HEART' States |
|---|---|---|---|
| 8 | Young shoot: prostrate hairs on tip | absent or very sparse | very dense |
| 11 | Young leaf: color of upper side of blade | dark copper-red (RHS 183B, 144A) | Green (RHS 148C) |
| 12 | Young leaf: prostrate hairs between main veins on lower side of blade | absent or very sparse | very dense |
| 57 | Mature leaf: blistering of upper side of blade | weak | medium to strong |

TABLE 3-continued

| No. | Characteristics | Reference variety 'SEKIREI' States | Present variety 'SUNNY HEART' States |
|---|---|---|---|
| 59 | Mature leaf: depth of upper lateral sinuses | medium | shallow |
| 90 | Berry: shape | narrow ellipsoid | broad ellipsoid |

A comparison with the reference variety 'KOTOPY' is as follows (average evaluation):

TABLE 4

| No. | Characteristics | Reference variety 'KOTOPY' States | Present variety 'SUNNY HEART' States |
|---|---|---|---|
| 11 | Young leaf: color of upper side of blade | light copper-red (RHS 148C, 178B) | Green (RHS 148C) |
| 12 | Young leaf: prostrate hairs between main veins on lower side | dense | very dense |
| 59 | Mature leaf: depth of upper lateral sinuses | medium | shallow |
| 66 | Mature leaf: prostrate hairs between main veins on lower side | medium | dense |
| 90 | Berry: shape | narrow ellipsoid | broad ellipsoid |

A comparison with both 'SEKIREI' and 'KOTOPY' is as follows (average evaluation):

TABLE 5

| No. | Characteristics | Reference variety 'SEKIREI' States | Reference variety 'KOTOPY' States | Present variety 'SUNNY HEART' States |
|---|---|---|---|---|
| 12 | Young leaf: color of upper side of blade | dark copper-red (RHS 183B, 144A) | light copper-red (RHS 148C, 178B) | green (RHS 148C) |
| 13 | Young leaf: prostrate hairs between main veins on lower side of blade | absent or very sparse | dense | very dense |
| 59 | Mature leaf: depth of upper lateral sinuses | medium | medium | shallow |
| 90 | Berry: shape | narrow ellipsoid | narrow ellipsoid | broad ellipsoid |

BRIEF DESCRIPTION OF THE DRAWINGS

In the accompanying drawings, which are as nearly true as is reasonable possible to make in a color illustration of this type.

Figure 1:
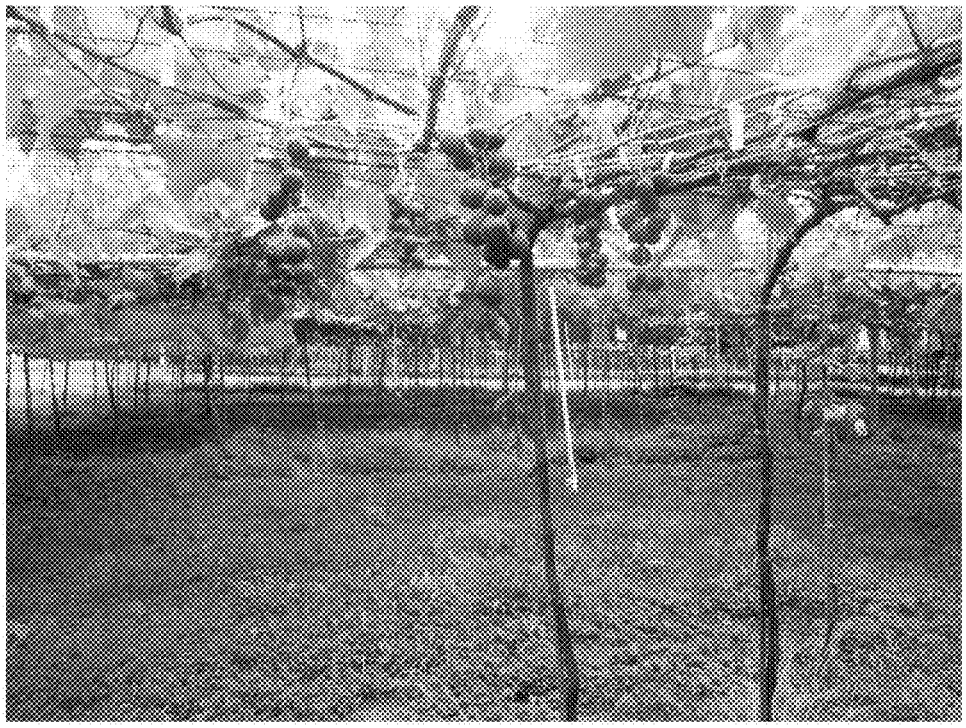
FIG. 1 is a color photograph showing a general view of the grapevine named 'SUNNY HEART' bearing vine.
Figure 2:
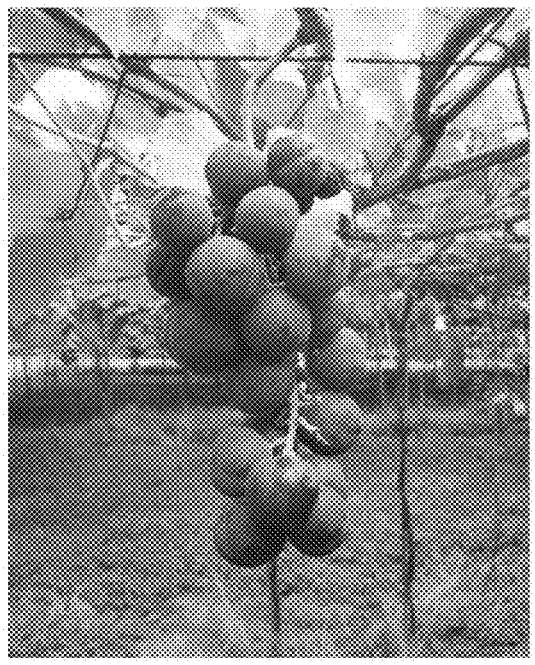
FIG. 2 is a color photograph showing a bunch of grapes on the vine of 'SUNNY HEART'.
Figure 3:
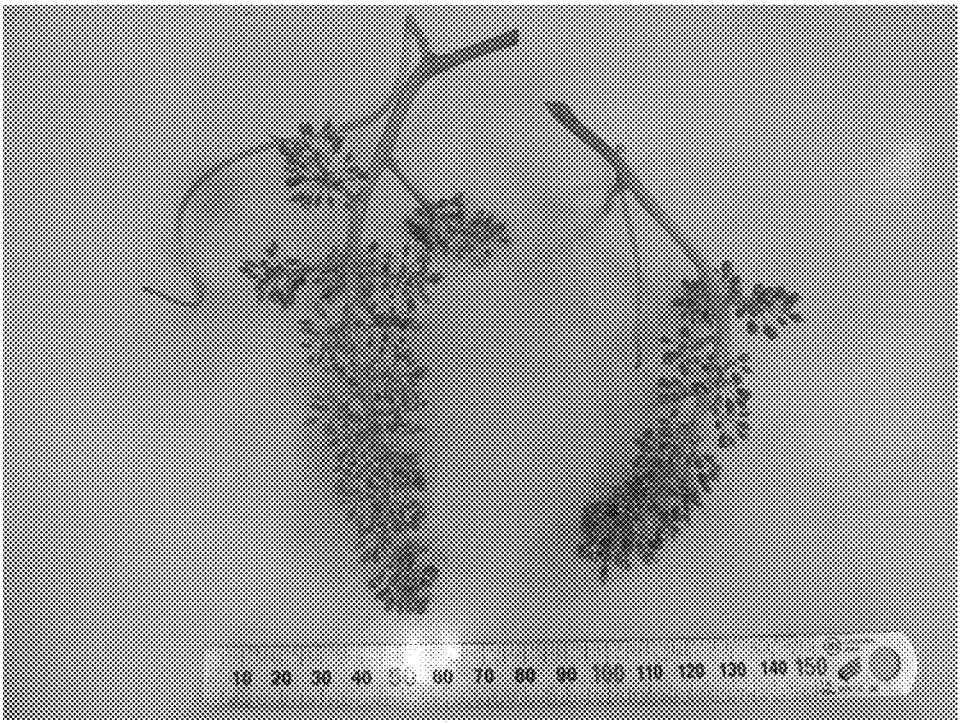
FIG. 3 is a color photograph showing flower clusters of 'SUNNY HEART'.
Figure 4:
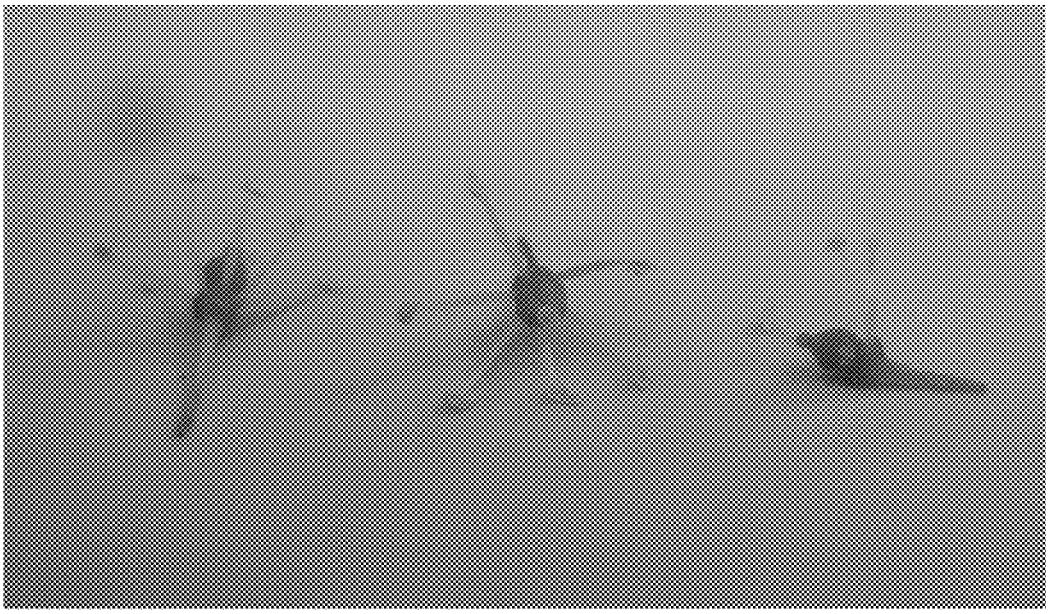
FIG. 4 is a color photograph showing flowers of 'SUNNY HEART'.
Figure 5:
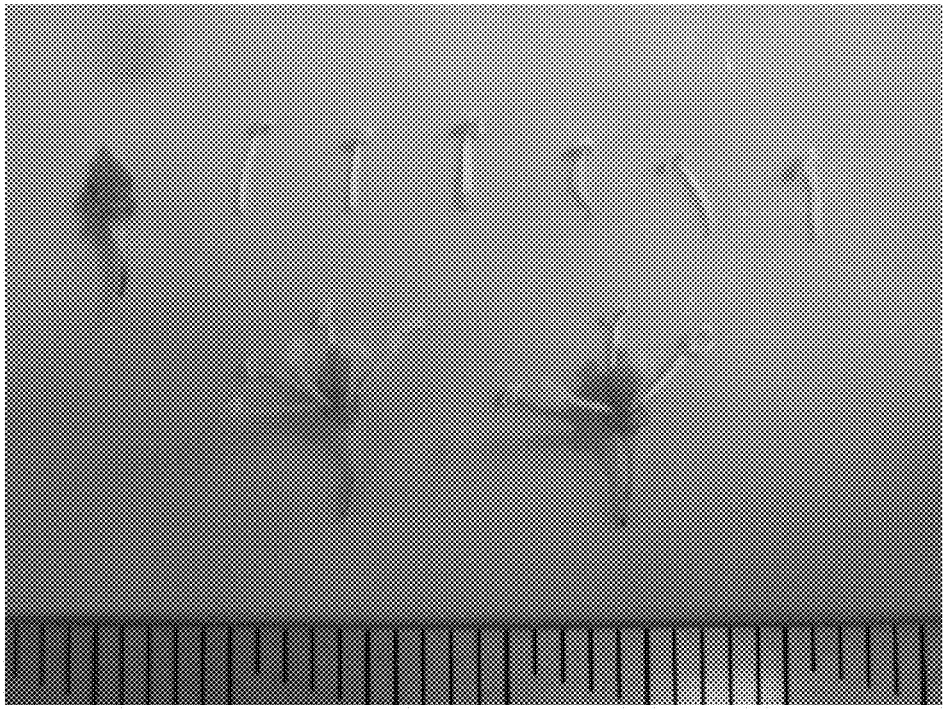
FIG. 5 is a color photograph showing the flowers and separated organs of 'SUNNY HEART'.
Figure 6:
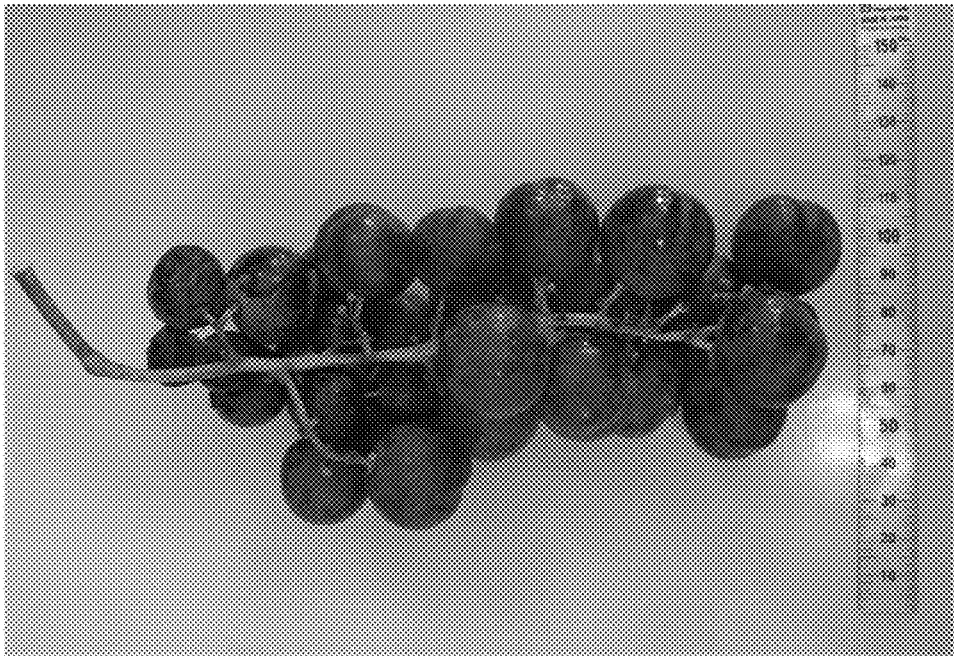
FIG. 6 is a color photograph showing a bunch of grapes cut from a vine of 'SUNNY HEART'.
Figure 7:
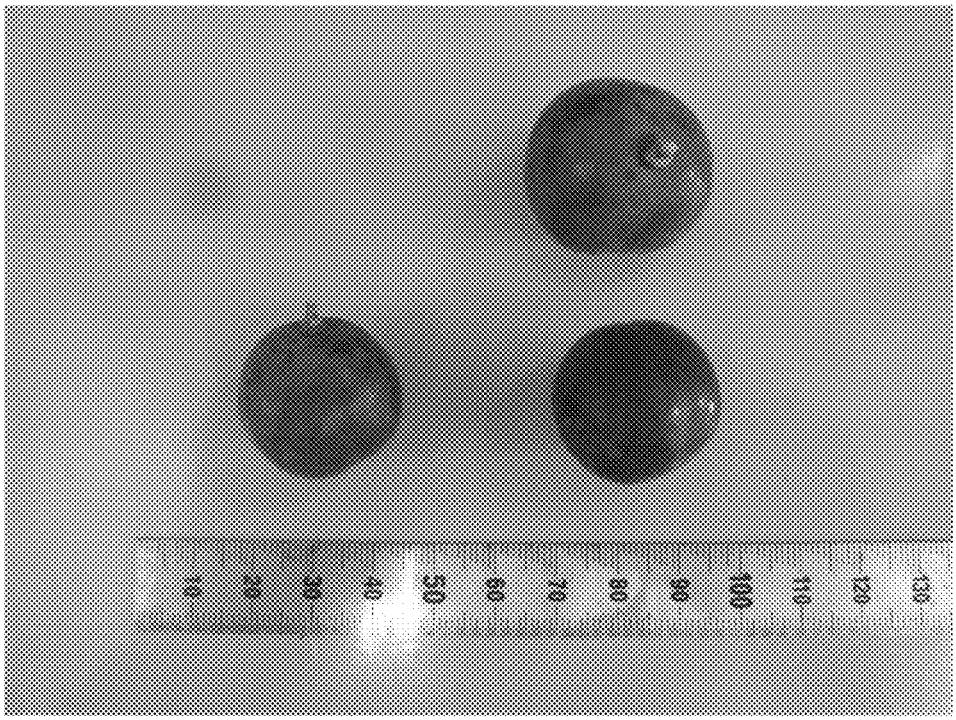
FIG. 7 is a color photograph showing berries of 'SUNNY HEART'.
Figure 8:
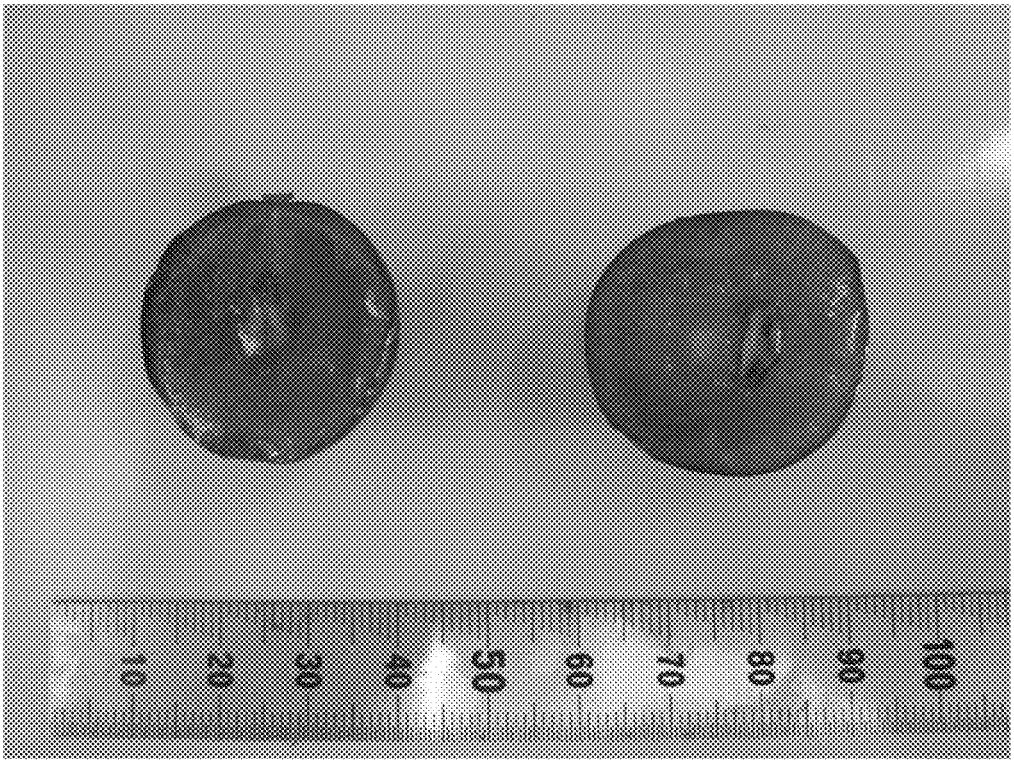
FIG. 8 is a color photograph showing cross-sections of berries of 'SUNNY HEART'.
Figure 9:
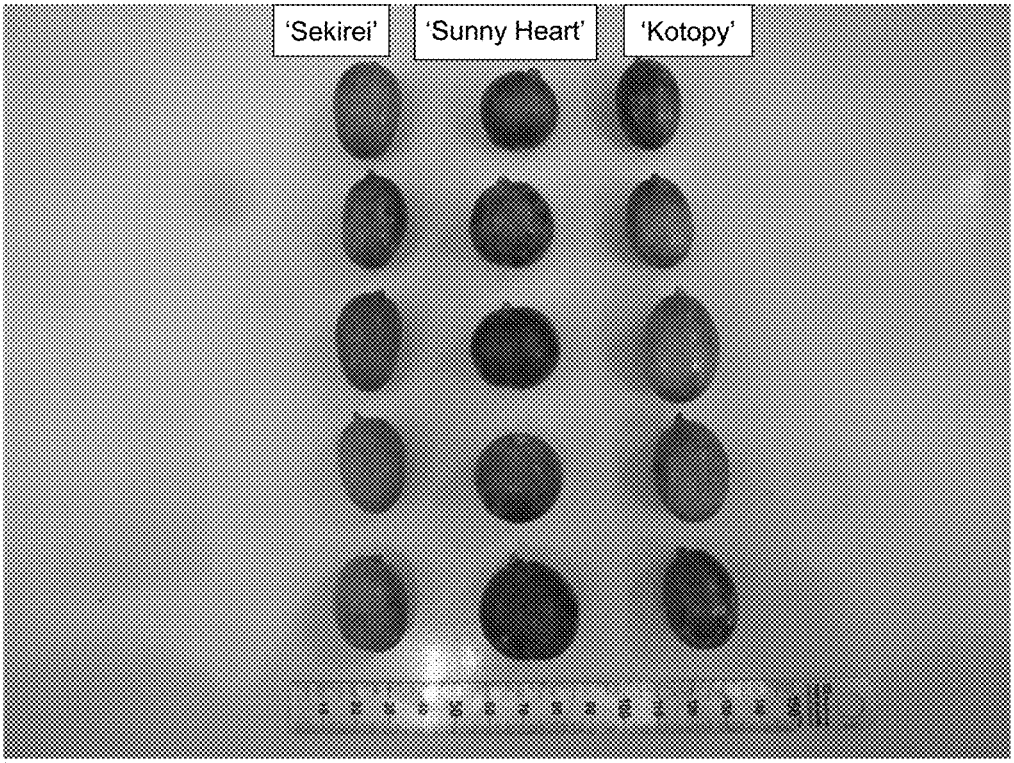
FIG. 9 is a color photograph showing berry shapes of 'SUNNY HEART' as well as 'SEKIREI' and 'KOTOPY' for comparison purposes.
Figure 10:
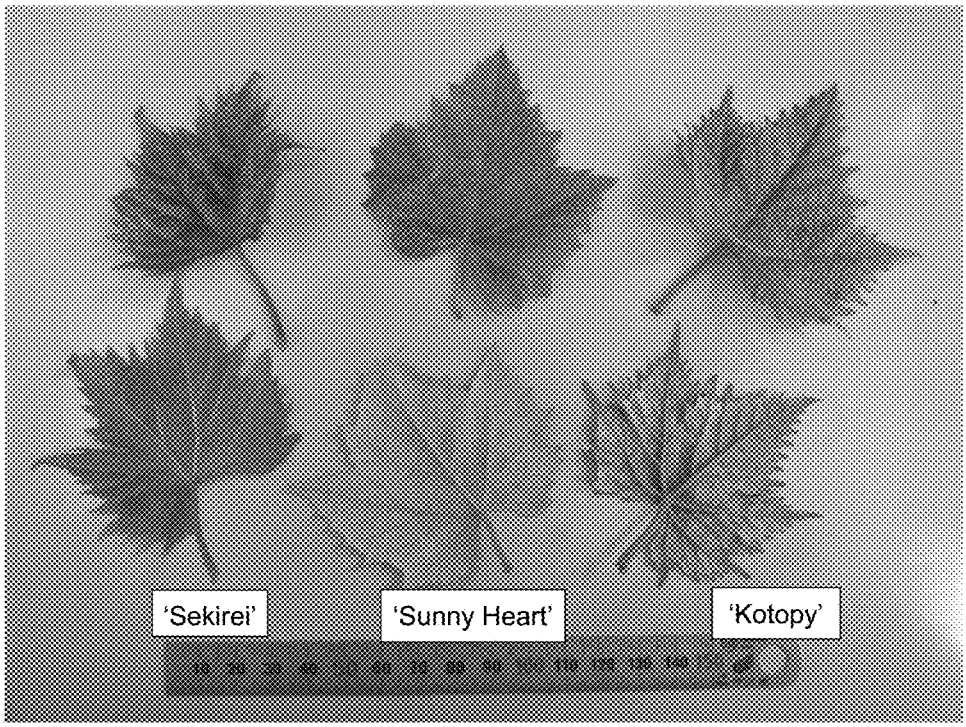
FIG. 10 is a color photograph showing the upper and lower sides of young leaves of 'SUNNY HEART' as well as 'SEKIREI' and 'KOTOPY' for comparison purposes.
Figure 11:
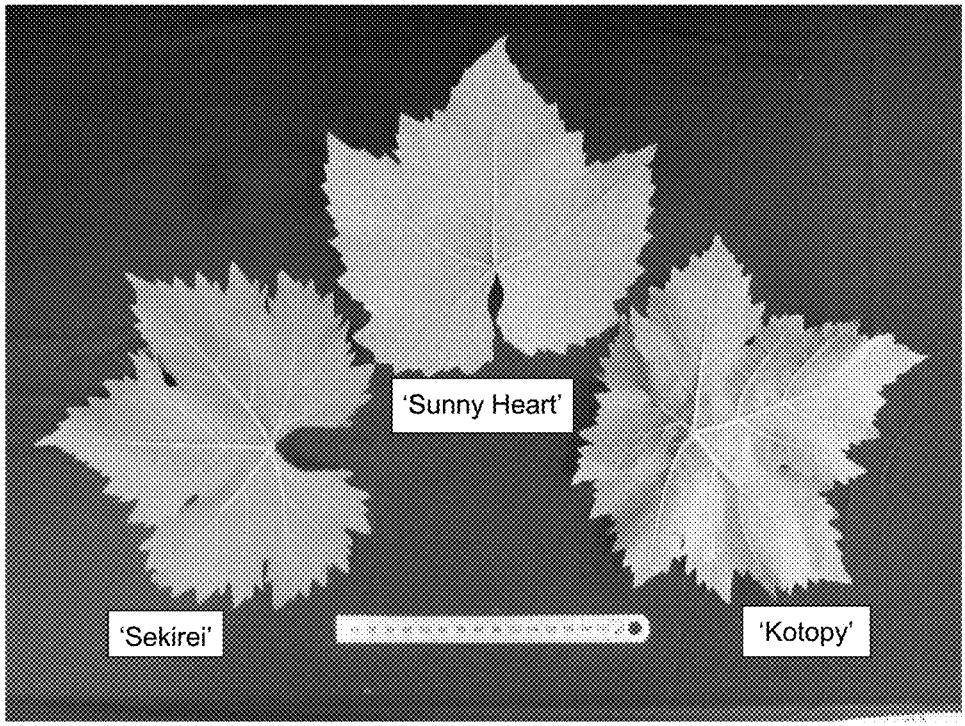
FIG. 11 is a color photograph showing the lower sides of mature leaves of 'SUNNY HEART' as well as 'SEKIREI' and 'KOTOPY' for comparison purposes.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'SUNNY HEART' plants evaluated in 2022 (including for the comparison with the reference plants 'SEKIREI' and 'KOTOPY'. Values as provided are averages.

The plants shown on the photographs were grown at Akitsu, Hiroshima, Japan. The plant is a 5-year grown plant. The young leaf and flower were photographed on May 29, 2023, the mature leaf was photographed on Jun. 29, 2023, and the bunch and berry was photographed on Sep. 15, 2023.

Colors are given according to The R.H.S. (Royal Horticultural Society) Color Chart, Sixth Edition (2015).

BOTANICAL DESCRIPTION

TABLE 6

| No. | Characteristics | States | Values |
|---|---|---|---|
| | Tree | | |
| 1 | Average height | | 180 cm |
| 2 | Average width | | 60 cm |
| 3 | Vigor | strong | |
| 4 | Trunk diameter (at a given height above soil line) | | 19.8 mm (at 20 cm above soil line) |
| 5 | Grown on rootstock | Yes | Teleki selectia Kober 5BB |
| 6 | Time of bud burst | early | early April (approx. Apr. 7) |
| | Young shoot | | |
| 7 | Openness of tip | wide open | |
| 8 | Prostrate hairs on tip | very dense | |
| 9 | Anthocyanin coloration of prostrate hairs on tip | absent or very weak | |
| 10 | Erect hairs on tip | absent or very sparse | |
| | Young leaf | | |
| 11 | Color of upper side of blade | green | 148C (RHS) |
| 12 | Prostrate hairs between main veins on lower side of blade | very dense | |

TABLE 6-continued

| No. | Characteristics | States | Values |
|---|---|---|---|
| 13 | Erect hairs on main veins on lower side of blade | absent or very sparse | |
| | Shoot | | |
| 14 | Average length of stem | | 186 cm |
| 15 | Average diameter of stem | | 22.0 mm |
| 16 | Texture of stem | rough | |
| 17 | Color of stem | brown | N200C, 200C (RHS) |
| 18 | Average length of branches | | 88 cm |
| 19 | Average diameter of branches | | 16.0 mm |
| 20 | Texture of branches | intermediate | |
| 21 | Color of branches | grey-brown | 199C, N199C (RHS) |
| 22 | Average length of shoots | | 5.9 m |
| 23 | Average diameter of shoots | | 9.8 mm |
| 24 | Texture of shoots | smooth | |
| 25 | Color of shoots | green | 144A (RHS) |
| 26 | Attitude (before tying) | semi-erect | |
| 27 | Color of dorsal side of internodes | green and red | 144A, 183B (RHS) |
| 28 | Color of ventral side of internodes | green | 144A (RHS) |
| 29 | Shoot: color of dorsal side of nodes | green and red | 144A, 183B (RHS) |
| 30 | Shoot: color of ventral side of nodes | green | 144A (RHS) |
| 31 | Erect hairs on internodes | absent or very sparse | |
| 32 | Length of tendrils | medium | 19.4 cm |
| | Flower | | |
| 33 | Average size of flower buds | | Width 1.5 mm, Length 2 mm |
| 34 | Color of flower buds | green | 144A (RHS) |
| 35 | Inflorescence | panicle | |
| 36 | Average number of petals on the flower | | 5 |
| 37 | Color of petals (top surface) | green | 144A (RHS) |
| 38 | Color of petals (bottom surface) | green | 144B (RHS) |
| 39 | Average petal size | | Width 0.4 mm, Length 2 mm |
| 40 | Length of flower clusters | medium | 19.3 cm |
| | Sexual organs | | |
| 41 | Sexual organs | fully developed stamens and fully developed gynoecium | |
| 42 | Average size of seeds | | Width 6.0 mm, Length 8.3 mm |
| 43 | Average number of seeds | | 2.4 |
| 44 | Average color of seeds | greyed-orange | 165B (RHS) |
| | Mature leaf | | |
| 45 | Leaf arrangement | Alternate | |
| 46 | Color of leaf (top surface) | green | 137B (RHS) |

TABLE 6-continued

| No. | Characteristics | States | Values |
|---|---|---|---|
| 47 | Color of leaf (bottom surface) | yellow-green | 148C (RHS) |
| 48 | Shape of leaf | wedged-shaped | |
| 49 | Texture of leaf (top surface) | medium to strong blistering | |
| 50 | Texture of leaf (bottom surface) | rough | |
| 51 | Vein color | yellow-green | 145C (RHS) |
| 52 | Average length of petiole | | 121 mm |
| 53 | Average diameter of petiole | | 3.9 mm |
| 54 | Color of petiole | yellow-green and greyed-purple | 145B(RHS), 183D(RHS) |
| 55 | Size of blade | Small to medium | 267 $cm^2$ |
| 56 | Shape of blade | wedged-shaped | |
| 57 | Blistering of upper side of blade | medium to strong | |
| 58 | Number of lobes | five | |
| 59 | Depth of upper lateral sinuses | shallow | 3.4 cm |
| 60 | Arrangement of lobes of upper lateral sinuses | open | |
| 61 | Arrangement of lobes of petiole sinus | slightly open | |
| 62 | Length of teeth | medium | 4.8 mm |
| 63 | Ratio length/width of teeth | small | 0.56 |
| 64 | Shape of teeth | mixture of both sides straight and both sides convex | |
| 65 | Proportion of main veins on upper side of blade with anthocyanin coloration | absent or very low | |
| 66 | Prostrate hairs between main veins on lower side of blade | dense | |
| 67 | Erect hairs on main veins on lower side of blade | absent or very sparse | |
| 68 | Length of petiole compared to length of middle vein | much shorter | 0.55 |
| | Fruit ripening | | |
| 69 | Date of first pick in specific location | approx. Sep. 5 | |
| 70 | Date of last pick in specific location | approx. Sep. 20 | |
| 71 | Time of beginning of berry ripening | medium to late | early August (approx. Aug. 5) |
| 72 | Pounds per bushels per acre | | About 890 pounds/acre |
| 73 | Storability of fruit | 12 days | |

TABLE 6-continued

| No. | Characteristics | States | Values |
|---|---|---|---|
| | Bunch | | |
| 74 | Average bunches per plant | | 5 |
| 75 | Average length of bunch | large | 183 mm |
| 76 | Average width of bunch | | 72 mm |
| 77 | Average weight of bunch | | 222.2 g |
| 78 | Average number of grapes per bunch | | 27.2 |
| 79 | Average length of peduncle | medium | 58 mm |
| 80 | Average diameter of peduncle | | 3.2 mm |
| 81 | Average color of peduncle | light red | 144A, 184D (RHS) |
| 82 | Size (peduncle excluded) | large | 183 mm |
| 83 | Density | medium | |
| 84 | Length of peduncle primary bunch | medium | 58 mm |
| 85 | Color of peduncle | light red | 144A, 184D (RHS) |
| | Berry | | |
| 86 | Average size of berry | | Width 24.8 mm, Length 26.0 mm |
| 87 | Color of berry skin | red | 187B (RHS) |
| 88 | Color of berry flesh | | 144D (RHS) |
| 89 | Size | large | 9.5 g |
| 90 | Shape | broad ellipsoid | |
| 91 | Color of skin (without bloom) | red | 187B (RHS) |
| 92 | Bloom | many | |
| 93 | Ease of detachment from pedicel | medium | |
| 94 | Thickness of skin | thin to medium | |
| 95 | separation of skin and flesh | difficult | |
| 96 | Anthocyanin coloration of flesh | absent or very weak | |
| 97 | Firmness of flesh | medium | |
| 98 | Character of flesh | collapse | |
| 99 | Sweetness of flesh juice | high | 20.7% |
| 100 | Juiciness of flesh | very juicy | |
| 101 | Particular flavor | Muscat | |
| 102 | Formation of seeds | complete | |
| | Woody shoot | | |
| 103 | Main color | orange brown | 177B (RHS) |
| | Ecotype | | |
| 104 | Flower shatter | medium | |

Other features of the plant are as follows:

*Disease resistance*.—Normal resistance was observed for pests and diseases in Akitsu, Hiroshima, Japan. Fungicide treatment was considered necessary against the following diseases: *Peronospora* (*Plasmopara*), *Oidium, Botrytis.*

I/we claim:

1. A new and distinct variety of grapevine named 'SUNNY HEART', substantially as described and illustrated herein.

* * * * *